(12) United States Patent
Chenault

(10) Patent No.: US 8,211,418 B2
(45) Date of Patent: *Jul. 3, 2012

(54) PROTEIN-BASED POLYMER TISSUE ADHESIVES FOR MEDICAL USE

(75) Inventor: Henry Keith Chenault, Hockessin, DE (US)

(73) Assignee: Actamax Surgerical Materials, LLC, Berkeley, CA (US)

( * ) Notice: Subject to any disclaimer, the term of this patent is extended or adjusted under 35 U.S.C. 154(b) by 84 days.

This patent is subject to a terminal disclaimer.

(21) Appl. No.: 12/904,230

(22) Filed: Oct. 14, 2010

(65) Prior Publication Data

US 2011/0027215 A1 Feb. 3, 2011

Related U.S. Application Data

(62) Division of application No. 11/289,169, filed on Nov. 29, 2005, now Pat. No. 7,837,986.

(60) Provisional application No. 60/632,272, filed on Dec. 1, 2004.

(51) Int. Cl.
*A61K 31/00* (2006.01)

(52) U.S. Cl. .................. 424/78.2; 424/78.08; 424/78.17

(58) Field of Classification Search .......................... None
See application file for complete search history.

(56) References Cited

U.S. PATENT DOCUMENTS

| 3,236,834 A | 2/1966 | Sofffer |
| 5,830,986 A | 11/1998 | Merrill et al. |
| 6,413,742 B1 | 7/2002 | Olsen et al. |
| 6,620,125 B1 | 9/2003 | Redl |
| 6,696,089 B2 | 2/2004 | Kabanov et al. |
| 2002/0022588 A1 | 2/2002 | Wilkie et al. |
| 2004/0063613 A1 | 4/2004 | Rolke et al. |

FOREIGN PATENT DOCUMENTS

| EP | 1004597 | 5/2000 |
| WO | WO 97/30103 | 8/1997 |
| WO | WO 99/66964 | 12/1999 |
| WO | WO 01/45761 | 6/2001 |

OTHER PUBLICATIONS

Otani et al., Journal of Biomedical Materials Research, vol. 31, 157-166 (1996).
Otani et al., Biomaterials, vol. 17, No. 14, 1387-1391 (1996).
International Search Report and Written Opinion, Application Serial No. PCT/U2005/043389.

*Primary Examiner* — James Rogers
(74) *Attorney, Agent, or Firm* — McCarter & English

(57) ABSTRACT

Tissue adhesives formed by crosslinking albumin and/or gelatin with certain polyamines and/or polycarboxylates using a water-soluble carbodiimide are disclosed. The use of the tissue adhesives for medical and veterinary applications such as topical wound closure; and surgical procedures, such as intestinal anastomosis, vascular anastomosis, tissue repair, and ophthalmic procedures; drug delivery; anti-adhesive applications; and as a bulking agent to treat urinary incontinence are described.

11 Claims, No Drawings

PROTEIN-BASED POLYMER TISSUE ADHESIVES FOR MEDICAL USE

CROSS-REFERENCE TO RELATED APPLICATION

This application is a Divisional of granted U.S. patent application Ser. No. 11/289,169 filed Nov. 29, 2005, which claims priority under 35 U.S.C. §119 from U.S. Provisional Application Ser. No. 60/632,272, filed Dec. 1, 2004.

FIELD OF THE INVENTION

The invention relates to the field of medical adhesives. More specifically, the invention relates to protein-based tissue adhesives formed by crosslinking albumin and/or gelatin with certain polyamines and/or certain polycarboxylates using a water-soluble carbodiimide.

BACKGROUND OF THE INVENTION

Tissue adhesives have many potential medical applications, including topical wound closure, supplementing or replacing sutures or staples in internal surgical procedures, adhesion of synthetic onlays or inlays to the cornea, drug delivery devices, and as anti-adhesion barriers to prevent post-surgical adhesions. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, the Fibrin-based adhesives do not covalently bind to the underlying tissue.

Protein-based tissue adhesives using albumin or gelatin are known. For example, Wilkie et al. (U.S. Patent Application Publication No. 2002/0022588) and Tammishetti et al. (WO 99/66964) describe tissue adhesives formed by crosslinking albumin with a carbodiimide. The addition of a polyamine, specifically, poly(lysine) or chitosan, or a polycarboxylate, specifically, citric acid or poly(acrylic acid), to increase the rate of crosslinking is also described in those disclosures. However, for use as a tissue adhesive for in vivo applications, such as intestinal anastomosis, adhesives with lower toxicity and enhanced adhesive strength are needed. The use of carbodiimides in the adhesive composition causes some toxicity problems. The toxicity problem is exacerbated by the use of a toxic polyamine such as poly(lysine). Chitosan is not soluble enough to be effective in increasing the adhesive properties of the adhesive.

Otani et al. (*J. Biomed. Mater. Res.* 31:157-166 (1996); and *Biomaterials* 17:1387-1391 (1996)) describe a tissue adhesive prepared by crosslinking gelatin and poly(L-glutamic acid) with a water-soluble carbodiimide. Although the adhesive is less toxic than the albumin-poly(lysine) adhesive described above, it lacks adhesive strength.

Therefore in the continuing search for new tissue adhesives for in vivo applications, such as intestinal anastomosis, the problem to be solved is to provide a protein-based tissue adhesive with lower toxicity and higher adhesive strength than those currently available.

Applicants have addressed the stated problem by discovering a tissue adhesive formed by crosslinking albumin and/or gelatin with certain polyamines and/or certain polycarboxylates using a water-soluble carbodiimide. The polyamines and polycarboxylates of the invention have low toxicity and provide a tissue adhesive with improved adhesive strength. Additionally, the polyamines and polycarboxylates of the invention permit the use of a lower carbodiimide concentration than can be used in the absence of the polyamines or polycarboxylates or in the presence of the polyamines or polycarboxylates known in the art, thereby further reducing the toxicity of the adhesive.

SUMMARY OF THE INVENTION

The invention provides a kit comprising:
A) a first vessel containing an aqueous solution comprising albumin, gelatin or a mixture thereof;
B) a second vessel containing an undissolved water-soluble carbodiimide; and
C) a third vessel, the contents of which comprise water;
provided that:
(i) the contents of at least one of the first or third vessels further comprise at least one of:
  (a) at least one polyamine selected from the group consisting of a water-dispersible multi-arm polyether amine, a water-dispersible aminoalkylated polysaccharide, and a water-dispersible aminoalkylated poly(vinyl alcohol), the total polyamine concentration being in the range of about 0.5% to about 20% by weight; or
  (b) at least one polycarboxylate selected from the group consisting of carboxymethyl cellulose, carboxymethyl dextran, and carboxymethyl starch, the total polycarboxylate concentration being in the range of about 0.5% to about 5% by weight; or
  (c) a mixture of said polyamine of (i)(a) having a total polyamine concentration in the range of about 0.5% to about 20% by weight and said polycarboxylate of (i)(b) having a total polycarboxylate concentration in the range of about 0.5% to about 5% by weight;
or
(ii) the kit further comprises a fourth vessel containing at least one of:
  (a) at least one polyamine selected from the group consisting of a water-dispersible multi-arm polyether amine, a water-dispersible aminoalkylated polysaccharide, and a water-dispersible aminoalkylated poly(vinyl alcohol) as a neat liquid; or
  (b) an aqueous polyamine solution comprising at least one polyamine selected from the group consisting of a water-dispersible multi-arm polyether amine, a water-dispersible aminoalkylated polysaccharide, and a water-dispersible aminoalkylated poly(vinyl alcohol),
    the total polyamine concentration being in the range of about 0.5% to about 20% by weight; or
  (c) an aqueous polycarboxylate solution comprising at least one polycarboxylate selected from the group consisting of carboxymethyl cellulose, carboxymethyl dextran, and carboxymethyl starch, the total polycarboxylate concentration being in the range of about 0.5% to about 5% by weight; or
  (d) an aqueous mixed polyamine/polycarboxylate solution comprising said at least one polyamine of (ii)(b) having a total polyamine concentration of about 0.5% to about 20% by weight, and said at least one polycarboxylate of (ii)(c) having a total polycarboxylate concentration of about 0.5% to about 5% by weight;
or
(iii) a combination of (i) and (ii);

provided further that:
(iv) if the aqueous solution in the first vessel of (A) comprises albumin, but not gelatin, then the concentration of albumin in the aqueous solution is about 25% to about 40% by weight;
(v) if the aqueous solution in the first vessel of (A) comprises gelatin, but not albumin, then the concentration of gelatin in the aqueous solution is about 15% to about 35% by weight; and
(vi) if the aqueous solution in the first vessel of (A) comprises a mixture of albumin and gelatin, then the total concentration of albumin and gelatin combined is about 15% to about 40% by weight.

In another embodiment, the invention provides a method for forming a coating on an anatomical site on tissue of a living organism comprising:
(A) forming on said site an aqueous mixture comprising:
  (i) at least one of albumin or gelatin;
  (ii) a water-soluble carbodiimide; and
  (iii) at least one of:
    (a) at least one polyamine selected from the group consisting of a water-dispersible multi-arm polyether amine, a water-dispersible aminoalkylated polysaccharide, and a water-dispersible aminoalkylated poly (vinyl alcohol); or
    (b) at least one polycarboxylate selected from the group consisting of carboxymethyl cellulose, carboxymethyl dextran, and carboxymethyl starch; and
  allowing said aqueous mixture to cure, thereby forming said coating; or
(B) forming an aqueous mixture comprising:
  (i) at least one of albumin or gelatin;
  (ii) a water-soluble carbodiimide; and
  (iii) at least one of:
    (a) at least one polyamine selected from the group consisting of a water-dispersible multi-arm polyether amine, a water-dispersible aminoalkylated polysaccharide, and a water-dispersible aminoalkylated poly (vinyl alcohol); or
    (b) at least one polycarboxylate selected from the group consisting of carboxymethyl cellulose, carboxymethyl dextran, and carboxymethyl starch; and
  applying said mixture to the site before the mixture completely cures, and allowing said aqueous mixture to cure completely, thereby forming said coating;
provided that:
  (i) if the aqueous mixture comprises albumin, but not gelatin, then the concentration of albumin in the aqueous mixture is about 20% to about 36% by weight;
  (ii) if the aqueous mixture comprises gelatin, but not albumin, then the concentration of gelatin in the aqueous mixture is about 12% to about 32% by weight;
  (iii) if the aqueous mixture comprises a mixture of albumin and gelatin, then the total concentration of albumin and gelatin combined is about 12% to about 36% by weight;
  (iv) the concentration of the water-soluble carbodiimide in the aqueous mixture is about 1% to about 10% by weight;
  (v) if the aqueous mixture comprises the polyamine, but not the polycarboxylate, then the concentration of the polyamine in the aqueous mixture is about 0.4% to about 20% by weight;
  (vi) if the aqueous mixture comprises the polycarboxylate, but not the polyamine, then the concentration of the polycarboxylate in the aqueous mixture is about 0.4% to about 5% by weight; and
  (vii) if the aqueous mixture comprises both the polyamine and the polycarboxylate, then the concentration of the polyamine in the aqueous mixture is about 0.4% to about 20% by weight and the concentration of the polycarboxylate is about 0.4% to about 5% by weight.

In another embodiment, the invention provides a method for bonding at least two anatomical sites together comprising:
A) forming an aqueous mixture in contact with at least two anatomical sites comprising:
  (i) at least one of albumin or gelatin;
  (ii) a water-soluble carbodiimide; and
  (iii) at least one of:
    (a) at least one polyamine selected from the group consisting of a water-dispersible multi-arm polyether amine, a water-dispersible aminoalkylated polysaccharide, and a water-dispersible aminoalkylated poly (vinyl alcohol); or
    (b) at least one polycarboxylate selected from the group consisting of carboxymethyl cellulose, carboxymethyl dextran, and carboxymethyl starch; and
B) allowing said aqueous mixture to cure;
provided that:
  (i) if the aqueous mixture comprises albumin, but not gelatin, then the concentration of albumin in the aqueous mixture is about 20% to about 36% by weight;
  (ii) if the aqueous mixture comprises gelatin, but not albumin, then the concentration of gelatin in the aqueous mixture is about 12% to about 32% by weight;
  (iii) if the aqueous mixture comprises a mixture of albumin and gelatin, then the total concentration of albumin and gelatin combined is about 12% to about 36% by weight;
  (iv) the concentration of the water-soluble carbodiimide in the aqueous mixture is about 1% to about 10% by weight;
  (v) if the aqueous mixture comprises the polyamine, but not the polycarboxylate, then the concentration of the polyamine in the aqueous mixture is about 0.4% to about 20% by weight;
  (vi) if the aqueous mixture comprises the polycarboxylate, but not the polyamine, then the concentration of the polycarboxylate in the aqueous mixture is about 0.4% to about 5% by weight; and
  (vii) if the aqueous mixture comprises both the polyamine and the polycarboxylate, then the concentration of the polyamine in the aqueous mixture is about 0.4% to about 20% by weight and the concentration of the polycarboxylate is about 0.4% to about 5% by weight.

In another embodiment, the invention provides a composition resulting from forming an aqueous mixture comprising:
(a) at least one of albumin or gelatin;
(b) a water-soluble carbodiimide; and
(c) at least one of:
  (i) at least one polyamine selected from the group consisting of a water-dispersible multi-arm polyether amine, a water-dispersible aminoalkylated polysaccharide, and a water-dispersible aminoalkylated poly (vinyl alcohol); or
  (ii) at least one polycarboxylate selected from the group consisting of carboxymethyl cellulose, carboxymethyl dextran, and carboxymethyl starch; and
allowing the aqueous mixture to cure;
provided that:
  (i) if the aqueous mixture comprises albumin, but not gelatin, then the concentration of albumin in the aqueous mixture is about 20% to about 36% by weight;

(ii) if the aqueous mixture comprises gelatin, but not albumin, then the concentration of gelatin in the aqueous mixture is about 12% to about 32% by weight;

(iii) if the aqueous mixture comprises a mixture of albumin and gelatin, then the total concentration of albumin and gelatin combined is about 12% to about 36% by weight;

(iv) the concentration of the water-soluble carbodiimide in the aqueous mixture is about 1% to about 10% by weight;

(v) if the aqueous mixture comprises the polyamine, but not the polycarboxylate, then the concentration of the polyamine in the aqueous mixture is about 0.4% to about 20% by weight;

(vi) if the aqueous mixture comprises the polycarboxylate, but not the polyamine, then the concentration of the polycarboxylate in the aqueous mixture is about 0.4% to about 5% by weight; and (vii) if the aqueous mixture comprises both the polyamine and the polycarboxylate, then the concentration of the polyamine in the aqueous mixture is about 0.4% to about 20% by weight and the concentration of the polycarboxylate is about 0.4% to about 5% by weight.

Methods for using the protein-based polymer tissue adhesive of the invention for topical wound closure, intestinal and vascular anastomoses, sealing corneal incisions, preventing adhesions, and drug delivery are also provided.

DETAILED DESCRIPTION OF THE INVENTION

The invention relates to a protein-based tissue adhesive formed by crosslinking albumin and/or gelatin with certain polyamines and/or certain polycarboxylates using a water-soluble carbodiimide. The tissue adhesive of the invention is useful as an adhesive for medical and veterinary applications including, but not limited to, topical wound closure, and surgical procedures, such as intestinal anastomosis, vascular anastomosis, tissue repair, and ophthalmic procedures. Additionally, the tissue adhesive may have utility in drug delivery, anti-adhesive applications, and as a bulking agent to treat urinary incontinence.

The following definitions are used herein and should be referred to for interpretation of the claims and the specification.

The term "polyamine" refers to a compound having at least two primary amine groups.

The term "polycarboxylate" refers to a compound having at least two carboxylic acid groups.

The term "water-dispersible, multi-arm polyether amine" refers to a branched polyether, wherein at least three of the branches ("arms") are terminated by a primary amine group, which is water soluble or able to be dispersed in water to form a colloidal suspension capable of reacting with a second reactant in aqueous solution.

The term "polyether" refers to a polymer having the repeat unit [—O—R]—, wherein R is a hydrocarbylene group having 2 to 5 carbon atoms.

The term "hydrocarbylene group" refers to a divalent group formed by removing two hydrogen atoms, one from each of two different carbon atoms, from a hydrocarbon.

The term "branched polyether" refers to a polyether having one or more branch points ("arms"), including star, dendritic, comb, and hyperbranched polyethers.

The term "dendritic polyether" refers to a highly branched polyether having a tree-like structure.

The term "comb polyether" refers to a polyether having a main chain with multiple trifunctional branch points from each of which a linear arm emanates.

The term "star polyether" refers to a polyether having a single branch point from which linear arms emanate.

The term "hyperbranched polyether" refers to a highly branched polyether having fewer branches and less regular branching than a dendritic polyether.

The term "water-dispersible aminoalkylated polysaccharide" refers to a polysaccharide which has at least two of its hydroxyl hydrogens replaced by hydrocarbyl groups bearing at least one primary amino group, wherein the hydrocarbyl groups are optionally substituted or optionally contain heteroatoms, and wherein the aminoalkylated polysaccharide is water soluble or able to be dispersed in water to form a colloidal suspension capable of reacting with a second reactant in aqueous solution.

The term "water-dispersible aminoalkylated poly(vinyl alcohol)" refers to a poly(vinyl alcohol) which has at least two of its hydroxyl hydrogens replaced by hydrocarbyl groups bearing at least one primary amino group, wherein the hydrocarbyl groups are optionally substituted or optionally contain heteroatoms, and wherein the aminoalkylated poly(vinyl alcohol) is water soluble or able to be dispersed in water to form a colloidal suspension capable of reacting with a second reactant in aqueous solution.

The term "hydrocarbyl group" refers to a univalent group formed by removing a hydrogen atom from a hydrocarbon.

The term "% by weight" as used herein refers to the weight percent relative to the total weight of the solution, unless otherwise specified.

The term "anatomical site" refers to any external or internal part of the body of humans or animals.

The term "tissue" refers to any tissue, both living and dead, in humans or animals.

The term "hydrogel" refers to a water-swellable polymeric matrix, consisting of a three-dimensional network of macromolecules held together by covalent or non-covalent crosslinks that can absorb a substantial amount of water to form an elastic gel.

The term "gene" refers to a nucleic acid fragment that effects the production of a specific protein, including regulatory sequences preceding (5' non-coding sequences) and following (3' non-coding sequences) the coding sequence.

The term "recombinant host cell", as used herein, refers to a cell that has been transformed using genetic engineering techniques to produce albumin or gelatin.

By medical application is meant medical applications as related to humans and for veterinary purposes.

The invention provides a tissue adhesive formed by crosslinking albumin and/or gelatin with certain polyamines and/or certain polycarboxylates using a water-soluble carbodiimide. Because these proteins contain both amine and carboxylic acid groups, they can be crosslinked with polyamines and/or polycarboxylates using carbodiimide crosslinking. The polyamines and polycarboxylates of the invention have low toxicity and provide a tissue adhesive with improved adhesive strength. Additionally, the polyamines and polycarboxylates of the invention permit the use of a lower carbodiimide concentration than can be used in the absence of the polyamines or polycarboxylates or in the presence of the polyamines or polycarboxylates known in the art, thereby further reducing the toxicity of the adhesive. The crosslinking reaction forms a hydrogel, which has many desirable characteristics as a tissue adhesive, including, but not limited to, improved adhesion and cohesion properties, crosslinks readily at body temperature, maintains dimensional stability initially, does not degrade rapidly, and has a lower toxicity to cells than other tissue adhesives that use carbodiimides.

Albumin:

Albumins are water-soluble proteins that are found in many animal tissues and fluids, such as milk, blood serum, and eggs. Most albumins are believed to be suitable for use in the invention. Of particular use are mammalian serum albumins and egg albumins (ovalbumins). Suitable mammalian serum albumins include, but are not limited to, bovine serum albumin, ovine (sheep) serum albumin, porcine (pig) serum albumin, human serum albumin, equine (horse) serum albumin, lapine (rabbit) serum albumin, rat serum albumin, and murine (mouse) serum albumin. Suitable egg albumins include, but are not limited to, chicken egg albumin. Mixtures of these albumins may also be used.

Albumin may be purified directly from tissues or fluids using methods known in the art, for example organic solvent precipitation or chromatographic methods, such as ion exchange or affinity chromatography. Additionally, albumin from many sources is available commercially from companies such as Sigma-Aldrich (St. Louis, Mo.).

The albumin may also be a recombinant albumin produced by a suitable recombinant host cell that expresses an albumin gene using standard recombinant DNA and molecular cloning techniques (Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989); Silhavy, T. J., Bennan, M. L. and Enquist, L. W., *Experiments with Gene Fusions*, Cold Spring Harbor Laboratory Cold Press Spring Harbor, N.Y. (1984); and Ausubel, F. M. et al., *Current Protocols in Molecular Biology*, published by Greene Publishing Assoc. and Wiley-Interscience (1987)). For example, the nucleotide sequences of the genes that encode bovine serum albumin (GenBank Accession. No. AF542068 and M73993), human serum albumin (Lawn et al. (*Nucleic Acids Res.* 9:6103-6114 (1981)), and ovalbumin (Woo et al. *Biochemistry* 20:6437-6446 (1981)) are known. These gene sequences may be expressed in a suitable host cell to produce the desired recombinant albumin. For example, recombinant human serum albumin may be expressed in *Escherichia coli*, as described by Lawn et al. (*Nucleic Acids Res.* 9:6103-6114 (1981)), in *Saccharomyces cerevisiae*, as described by Kalman et al. (*Nucleic Acids Res.* 18:6075-6081 (1990)), or in transgenic mice, as described by Shani et al. (*Transgenic Research* 1:195-208 (1992)). Additionally, recombinant human serum albumin is available commercially from companies such as GTC Biotherapeutics (Framingham, Mass.) and Delta Biotechnology Limited (Nottingham, UK).

Additionally, a recombinant albumin variant may be used, in which one or more amino acid residues are inserted, deleted, or substituted using standard techniques, such as site-directed mutagenesis. Suitable albumin variants have an amino acid sequence that has a percent identity of at least about 70%, or at least about 80%, or at least about 85%, or at least about 90%, or at least about 95% relative to the native albumin sequence. The "percent identity", which is a relationship between two or more polypeptide sequences, can be readily calculated by known methods, including but not limited to, those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

In the invention, the albumin is used in the form of an aqueous solution. The albumin is added to water to give a concentration of about 25% to about 40% by weight relative to the total weight of the solution. The optimal concentration to be used depends on the application and on the concentrations of the water-soluble carbodiimide and the polyamine and/or polycarboxylate used, as described below, and can be readily determined by one skilled in the art using routine experimentation.

For use on living tissue, it is preferred that the aqueous solution comprising the albumin be sterilized to prevent infection. Any suitable sterilization method known in the art that does not degrade the protein may be used, including, but not limited to, gamma irradiation, ethylene oxide sterilization, or ultra-filtration through a 0.2 µm pore membrane.

The aqueous solution comprising the albumin may further comprise various additives depending on the intended application. For example, the solution may optionally include at least one pH modifier to adjust the pH of the solution. Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, nitrogen-containing compounds other than primary and secondary amines, and basic carbonates and phosphates.

The aqueous solution comprising the albumin may optionally include at least one viscosity modifier. The viscosity modifier may be selected from among known viscosity modifiers, including, but not limited to, polysaccharides and derivatives thereof, such as starch or hydroxyethyl cellulose.

The aqueous solution comprising the albumin may optionally include at least one antimicrobial agent. Suitable antimicrobial agents are well known in the art. Examples of suitable antimicrobials include, but are not limited to, antibiotics such as tetracycline, ampicillin, vancomycin, polymyxin B, ciprofloxacin, teicoplanin, cefoxitin, gentamicin, and tobramycin.

The aqueous solution comprising the albumin may also optionally include at least one colorant to enhance the visibility of the solution. Suitable colorants include dyes, pigments, and natural coloring agents. Examples of suitable colorants include, but are not limited to, FD&C dyes and FD&C lakes, such as FD&C Violet No. 2, FD&C Yellow No. 6, FD&C Red No. 3, FD&C Blue No. 2; beetroot red; canthaxanthin, chlorophyll; eosin; saffron; and carmine.

The aqueous solution comprising the albumin may also optionally include at least one surfactant. Surfactant, as used herein, refers to a compound that lowers the surface tension of water. The surfactant may be an ionic surfactant, such as sodium lauryl sulfate, and octanoic acid; or a neutral surfactant, such as polyoxyethylene ethers, polyoxyethylene esters, and polyoxyethylene sorbitan.

Additionally, the aqueous solution comprising the albumin may optionally include anti-inflammatory agents, such as indomethacin, salicylic acid acetate, ibuprophen, sulindac, piroxicam, and naproxen; thrombogenic agents, such as thrombin, fibrinogen, homocysteine, and estramustine; healing promoters, such as chitosan; and radio-opaque compounds, such as barium sulfate and gold particles.

Gelatin:

Gelatins are water-soluble proteins that are obtained from animal tissues, such as bone and skin, by acid or alkaline treatment. Gelatins suitable for use in the invention include, but are not limited to, gelatins obtained from bovine skin, porcine skin, and fish skin. Gelatins are available commercially from companies such as Sigma-Aldrich. Commercial gelatins are designated by Bloom number, which is an indication of the strength of the gel produced. The higher the Bloom number, the stronger the gelatin gel.

The gelatin may also be a recombinant gelatin produced by a suitable recombinant host cell that expresses a gelatin gene, as described above. For example, recombinant gelatin may be prepared as described by Olsen et al. in U.S. Pat. No. 6,413,742. Additionally, a recombinant gelatin variant may be used, in which one or more amino acid residues are inserted, deleted, or substituted using standard techniques, such as site-directed mutagenesis. Suitable gelatin variants have an amino acid sequence that has a percent identity of at least about 70%, or at least about 80%, or at least about 85%, or at least about 90%, or at least about 95% relative to the native gelatin sequence.

In the invention, the gelatin is used in the form of an aqueous solution. The gelatin is added to water to give a concentration of about 15% to about 35% by weight relative to the total weight of the solution. The optimal concentration to be used depends on the application and on the concentrations of the water-soluble carbodiimide and the polyamine and/or polycarboxylate used, as described below, and can be readily determined by one skilled in the art using routine experimentation.

For use on living tissue, it is preferred that the aqueous solution comprising the gelatin be sterilized to prevent infection. Any of the methods described above for sterilizing the albumin solution may be used.

The aqueous solution comprising the gelatin may further comprise various additives. Any of the additives described above for the albumin solution may be used.

Additionally, an aqueous solution comprising a mixture of albumin and gelatin may be used in the invention. In the mixture, the total concentration of albumin and gelatin combined is from about 15% to about 40% by weight relative to the total weight of the solution. Preferably, the concentration of albumin in the mixture is from about 1% to about 39% by weight and the concentration of gelatin is from about 1% to about 34% by weight. The aqueous solution comprising the albumin, the aqueous solution comprising the gelatin, and the aqueous solution comprising a mixture of albumin and gelatin are herein referred to as "the protein solution".

Polyamines:

The polyamines of the invention contain at least two primary amine groups and were selected based on their low toxicity and their ability to produce a tissue adhesive with good adhesive strength. Additionally, the use of these polyamines enables the use of a lower carbodiimide concentration than can be used in the absence of the polyamines or polycarboxylates or in the presence of the polyamines or polycarboxylates known in the art, thereby further reducing the toxicity of the adhesive. The polyamines of the invention are a water-dispersible multi-arm polyether amine, a water-dispersible aminoalkylated polysaccharide, and a water-dispersible aminoalkylated poly(vinyl alcohol). Mixtures of these polyamines may also be used.

Water-Dispersible Multi-Arm Polyether Amines:

The multi-arm polyether amines are water-dispersible polyethers having the repeat unit [—O—R]—, wherein R is a hydrocarbylene group having 2 to 5 carbon atoms. The multi-arm polyether amines of the invention include, but are not limited to, dendritic, comb, and star polyethers wherein at least three of the arms are terminated by a primary amine group. The multi-arm polyether amines have a weight-average molecular weight of about 450 to about 200,000 Daltons, in addition from about 2,000 to about 100,000 Daltons. Suitable examples of water-dispersible, multi-arm polyether amines include, but are not limited to, amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star copolymers of ethylene oxide and propylene oxide, amino-terminated dendritic copolymers of ethylene oxide and propylene oxide, amino-terminated comb copolymers of ethylene oxide and propylene oxide, amino-terminated star copolymers of ethylene oxide and trimethylene oxide, amino-terminated dendritic copolymers of ethylene oxide and trimethylene oxide, amino-terminated comb copolymers of ethylene oxide and trimethylene oxide, amino-terminated star copolymers of ethylene oxide and butylene oxide, amino-terminated dendritic copolymers of ethylene oxide and butylene oxide, amino-terminated comb copolymers of ethylene oxide and butylene oxide, amino-terminated star copolymers of ethylene oxide and tetrahydrofuran, amino-terminated dendritic copolymers of ethylene oxide and tetrahydrofuran, amino-terminated comb copolymers of ethylene oxide and tetrahydrofuran, amino-terminated dendritic polyamidoamines, sold under the trade name Starburst® Dendrimers (available from Sigma-Aldrich, St Louis, Mo.); polyoxyalkylene triamines, sold under the trade name Jeffamine® triamines, by Huntsman LLC (Houston, Tex.), and mixtures thereof. Examples of star polyethylene oxide amines, include, but are not limited to, various multi-arm polyethylene glycol amines, available from Nektar Transforming Therapeutics (Huntsville, Ala.), and star polyethylene glycols having 3, 4, or 8 arms terminated with primary amines. The 8-arm star polyethylene glycol octamine (referred to herein as 8PEGA) is available from Nektar Transforming Therapeutics. Examples of suitable Jeffamine® triamines include, but are not limited to, Jeffamine® T-403 (CAS No. 39423-51-3), Jeffamine® T-3000 (CAS No. 64852-22-8), and Jeffamine® T-5000 (CAS No. 64852-22-8). In one embodiment, the water-dispersible multi-arm polyether amine is an eight-arm polyethylene glycol having eight arms terminated by a primary amine group and having a molecular weight of 10,000 Daltons (available from Nektar Transforming Therapeutics).

These multi-arm polyether amines are either available commercially, as noted above, or may be prepared using methods known in the art. For example, multi-arm polyethylene glycols, wherein at least three of the arms are terminated by a primary amine group, may be prepared by putting amine ends on multi-arm polyethylene glycols (e.g., 3, 4 and 8-arm star polyethylene glycols, available from Nektar Transforming Therapeutics) using the method described by Bückmann et al. (*Makromol. Chem.* 182:1379-1384 (1981)). In that method, the multi-arm polyethylene glycol is reacted with thionyl bromide to convert the hydroxyl groups to bromines, which are then converted to amines by reaction with ammonia at 100° C. The method is broadly applicable to the preparation of other multi-arm polyether amines. Other methods that may be used for preparing multi-arm polyether amines are described by Merrill et al. in U.S. Pat. No. 5,830, 986, and by Chang et al. in WO 97/30103.

Water-Dispersible Aminoalkylated Polysaccharides:

The water-dispersible aminoalkylated polysaccharides are polysaccharides that have at least two of their hydroxyl hydrogens replaced by hydrocarbyl groups bearing at least one primary amino group and are water soluble or able to be dispersed in water to form a colloidal suspension capable of reacting with a second reactant in aqueous solution. The hydrocarbyl groups may be linear, branched, or cyclic, aliphatic or aromatic groups. The hydrocarbyl groups may be optionally substituted or optionally contain heteroatoms, such as oxygen, sulfur, silicon, or nitrogen. Preferably, the water-dispersible aminoalkylated polysaccharides have a weight-average molecular weight between about 2,000 and about 1,000,000 Daltons.

Suitable examples of water-dispersible aminoalkylated polysaccharides include, but are not limited to, aminoalkyl starch, aminoalkyl cellulose, aminoalkyl inulin, aminoalkyl dextran, aminoalkyl amylose, aminoalkyl amylopectin, aminoalkyl laminarin, aminoalkyl hydroxyethyl starch, aminoalkyl hydroxyethyl cellulose, aminoalkyl hydroxyethyl inulin, aminoalkyl hydroxyethyl dextran, aminoalkyl hydroxyethyl amylose, aminoalkyl hydroxyethyl amylopectin, aminoalkyl hydroxyethyl laminarin, and mixtures thereof, wherein the aminoalkyl groups contain from 2 to about 20 carbon atoms, are optionally substituted, optionally contain heteroatoms, and contain at least one primary amine group. Examples of suitable aminoalkyl groups include, but are not limited to 2-aminoethyl and 3-aminopropyl.

Water-dispersible aminoalkylated polysaccharides may be prepared using methods known in the art. For example, water-dispersible aminoalkylated polysaccharides, wherein at least three of the arms are terminated by a primary amine group, may be prepared by putting aminoalkyl groups onto polysaccharides using the method described by Verraest et al. (*Starch/Stärke* 48:191-195 (1996)). In that method, the polysaccharide is partially cyanoethylated by reaction with acrylonitrile, and the nitrile groups are reduced to primary amines. The method is broadly applicable to the preparation of other aminoalkylated polysaccharides. Similar methods that may used for preparing aminoalkylated polysaccharides are described by Daly and Munir (*J. Polym. Sci., Polym. Chem. Ed.* 22:975-984 (1984)), Mann et al. (*Bioconjugate Chem.* 3:154-159 (1992)), and Soffer (U.S. Pat. No. 3,236,834).

Water-Dispersible Aminoalkylated Poly(Vinyl Alcohols):

The water-dispersible aminoalkylated poly(vinyl alcohols) are poly(vinyl alcohols) that have at least two of their hydroxyl hydrogens replaced by hydrocarbyl groups bearing at least one primary amino group, and are water soluble or able to be dispersed in water to form a colloidal suspension capable of reacting with a second reactant in aqueous solution. The hydrocarbyl groups may be linear, branched, or cyclic, aliphatic or aromatic groups. The hydrocarbyl groups may be optionally substituted or optionally contain heteroatoms, such as oxygen, sulfur, silicon, or nitrogen. Preferably, the degree of hydrolysis of the poly(vinyl alcohol) is from about 60% to about 100%, more preferably from about 80% to about 100%, most preferably from about 95% to about 99%. Preferably, the weight-average molecular weight of the water-dispersible aminoalkylated poly(vinyl alcohol) is between about 2,000 and about 1,000,000 Daltons.

Suitable examples of water-dispersible aminoalkylated poly(vinyl alcohols) include, but are not limited to, aminoalkyl poly(vinyl alcohol), aminoalkyl poly(vinyl alcohol) copolymers, poly(vinyl alcohol) derivatized with ω-amino acetal groups, poly(vinyl alcohol) copolymers derivatized with ω-amino acetal groups, aminoalkyl poly(vinyl alcohol) derivatized with ω-amino acetal groups, aminoalkyl poly(vinyl alcohol) copolymers derivatized with ω-amino acetal groups, aminoalkyl hydroxyethyl poly(vinyl alcohol), and mixtures thereof, wherein the aminoalkyl groups and ω-amino acetal groups contain from 2 to about 20 carbon atoms, are optionally substituted, optionally contain heteroatoms, and contain at least one primary amine group. Examples of useful aminoalkyl groups include, but are not limited to 2-aminoethyl and 3-aminopropyl. An example of a useful ω-amino acetal group is 4-aminobutyral acetal. The aminoalkyl poly(vinyl alcohol) copolymers and poly(vinyl alcohol) copolymers derivatized with ω-amino acetal groups comprise an amount of comonomer units equal to between about 1 mole percent and about 100 mole percent of the amount of vinyl alcohol monomer units. Suitable comonomers include, but are not limited to, vinyl acetate, methyl vinyl ether, N-vinyl formamide, ethylene, propylene, 1-butene, methyl acrylate, acrylic acid, methyl methacrylate, methacrylic acid, maleic acid, fumaric acid, itaconic acid, and mixtures thereof.

Water-dispersible aminoalkylated poly(vinyl alcohols) may be prepared using methods known in the art. For example, water-dispersible aminoalkylated poly(vinyl alcohol), wherein at least three of the arms are terminated by a primary amine group, may be prepared by putting aminoalkyl groups onto poly(vinyl alcohol) using the method described by Alexandru et al. (*J. Polym. Sci.* 59:129-137 (1962)). In that method, the poly(vinyl alcohol) is partially cyanoethylated by reaction with acrylonitrile, and the nitrile groups are reduced to primary amines.

The polyamine may be a component of the protein solution, or may be present in a separate solution, either as a neat liquid (i.e., undiluted pure liquid) or as an aqueous solution, referred to herein as the aqueous polyamine solution; or in the water used to hydrate the water-soluble carbodiimide, as described below. When contained in the protein solution or as a separate aqueous solution, or in the water used to hydrate the water-soluble carbodiimide, the concentration of the polyamine is about 0.5% to about 20% by weight relative to the total weight of the solution. If a mixture of different polyamines is used, the total polyamine concentration is about 0.5% to about 20% by weight. The optimal concentration to be used depends on the application and on the concentrations of the albumin and/or gelatin, the polycarboxylate (if present), and the water-soluble carbodiimide used, as described below.

For use on living tissue, it is preferred that the aqueous polyamine solution be sterilized to prevent infection. Any of the methods described above for sterilizing the albumin solution may be used.

The aqueous polyamine solution may further comprise various additives. Any of the additives described above for the albumin solution may be used.

Polycarboxylates:

The polycarboxylates of the invention contain at least two carboxylic acid groups and were selected based on their low toxicity and their ability to produce a tissue adhesive with good adhesive strength. The polycarboxylates of the invention are carboxymethyl cellulose, carboxymethyl dextran, and carboxymethyl starch. Mixtures of these polycarboxylates may also be used. Carboxymethyl cellulose and carboxymethyl dextran are available commercially from companies such as Sigma-Aldrich. Carboxymethyl starch may be prepared using methods known in the art (Zhang, et al. *J. Appl. Polym. Sci.* 89:3016-3020 (2003); Lazik, et al. *J. Appl.*

Polym. Sci. 86:743-752 (2002); Tijsen, et al. *Carbohydr. Polym.* 45:219-226 (2001); and Stojanovic, et al. *Starch/Stärke* 52:413-419 (2000)).

The polycarboxylate may be a component of the protein solution, or may be present in a separate aqueous solution, referred to herein as the aqueous polycarboxylate solution; or in the water used to hydrate the water-soluble carbodiimide, as described below. When contained in the protein solution or as a separate aqueous solution, or in the water used to hydrate the water-soluble carbodiimide, the concentration of the polycarboxylate is about 0.5% to about 5% by weight relative to the total weight of the solution. If a mixture of different polycarboxylates is used, the total polycarboxylate concentration is about 0.5% to about 5% by weight. The optimal concentration to be used depends on the application and on the concentrations of the albumin and/or gelatin, the polyamine (if present), and the water-soluble carbodiimide used, as described below.

For use on living tissue, it is preferred that the aqueous polycarboxylate solution be sterilized to prevent infection. Any of the methods described above for sterilizing the albumin solution may be used.

The aqueous polycarboxylate solution may further comprise various additives. Any of the additives described above for the albumin solution may be used.

The polycarboxylate may be used in combination with a polyamine. In that embodiment, the polycarboxylate and the polyamine may be components of the protein solution, or may be present in a separate aqueous solution, referred to herein as the aqueous mixed polyamine/polycarboxylate solution; or in the water used to hydrate the water-soluble carbodiimide. Additionally, the polycarboxylate may be a component of the protein solution, or may be present in a separate aqueous solution; or in the water used to hydrate the water-soluble carbodiimide, and the polyamine may be provided as a neat liquid, or in a separate aqueous solution. Alternatively, the polyamine may be a component of the protein solution, or in the water used to hydrate the water-soluble carbodiimide, and the polycarboxylate may be provided in a separate aqueous solution. In the aqueous mixed polyamine/polycarboxylate solution, the concentration of the polyamine is from about 0.5% to about 20% by weight and the concentration of the polycarboxylate is from about 0.5% to about 5% by weight relative to the total weight of the solution.

For use on living tissue, it is preferred that the aqueous mixed polyamine/polycarboxylate solution be sterilized to prevent infection. Any of the methods described above for sterilizing the albumin solution may be used.

The aqueous mixed polyamine/polycarboxylate solution may further comprise various additives. Any of the additives described above for the albumin solution may be used.

Water-Soluble Carbodiimides:

Carbodiimides are crosslinking reagents that react with carboxyl groups to form a reactive intermediate, which subsequently reacts with a nucleophile, such as amine, hydroxyl, and sulfhydryl groups, to form a covalent bond. Carbodiimides are reactive over a broad pH range (i.e., from 1.0 to 9.5). The reaction rate is slow at alkaline pH (i.e., pH>8.0), but increases at lower pH. However, at low pH the carbodiimide hydrolyzes, thereby reducing its effectiveness. Therefore, the reaction is optimally carried out at a pH between about 5.0 and about 7.0.

The carbodiimides of the invention are water-soluble carbodiimides having one of the general structures 1 or 2:

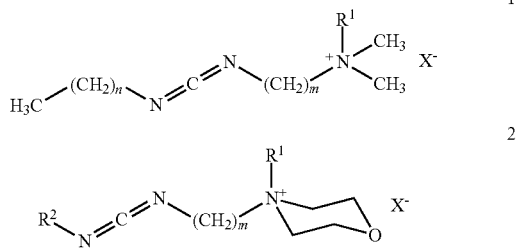

wherein $R^1$=hydrogen, methyl or ethyl, $R^2$=methyl, ethyl, propyl, isopropyl or cyclohexyl, n=0, 1 or 2, m=1, 2 or 3, and $X^-$=chloride, bromide, iodide, acetate, sulfate, hydrogen sulfate, methyl sulfate, methanesulfonate, ethanesulfonate, 1-propanesulfonate, 2-propanesulfonate, 1-butanesulfonate, benzenesulfonate, p-toluenesulfonate, or perchlorate. Examples of suitable water-soluble carbodiimides include, but are not limited to, 1-ethyl-3-(3-dimethylaminopropyl)-carbodiimide (EDC), 1-[3-(dimethylamino)propyl]-3-ethylcarbodiimide methiodide, and 1-cyclohexyl-3-(2-morpholinoethyl)carbodiimide metho-p-toluenesulfonate (CMC), which are available commercially from companies such as Sigma-Aldrich and Advanced ChemTech Inc. (Louisville, Ky.).

Generally, carbodiimides are not stable in aqueous solution because they are subject to hydrolysis. Therefore, they are provided in dry form (i.e., undissolved) and may be hydrated at the time of use by adding water. Preferably, distilled or deionized water is used. The concentration of water-soluble carbodiimide in the resulting aqueous solution is from about 5% to about 50% by weight relative to the weight of the solution. Typically, the protein solution and the water-soluble carbodiimide solution (5 to 25 wt %) are mixed in a 4:1 to 5:1 volume ratio. If a more concentrated water-soluble carbodiimide solution (e.g., 50 wt %) is used, the volume ratio of protein solution to water-soluble carbodiimide solution may be increased to about 10:1 to about 50:1.

For use on living tissue, it is preferred that the undissolved water-soluble carbodiimide be sterilized to prevent infection. Any of the methods described above for sterilizing the albumin solution may be used. It is also preferred that the water used to hydrate the carbodiimide be sterilized using any of the aforementioned methods. Additionally, the water may be sterilized by autoclaving at about 121° C.

The water used to hydrate the water-soluble carbodiimide may contain the polyamine and/or the polycarboxylate, as described above. If the water contains the polycarboxylate, it is preferred that the pH of the water be basic to prevent premature reaction between the polycarboxylate and the water-soluble carbodiimide. The pH of the water may be adjusted using any of the basic pH modifiers described above for the albumin solution. The preferred pH is at least about 8.0. To ensure that the pH of the solution formed by mixing the basic solution comprising the carbodiimide and the polycarboxylate with the protein solution is in the proper range for the crosslinking reaction, (i.e., 5.0 to 7.0), the pH of the protein solution is made acidic using any of the acidic pH modifiers described above for the albumin solution. Alternatively, the pH of the basic solution comprising the carbodiimide and the polycarboxylate may be adjusted to the desired pH by the addition of an acidic solution, containing an acidic pH modifier such as that described above, just prior to mixing with the protein solution. Additionally, the pH of the solution formed by mixing the basic solution comprising the carbodiimide and the polycarboxylate with the protein solution may be adjusted after mixing.

Additionally, various additives may be included in the water used to hydrate the undissolved water-soluble carbodiimide. Any of the additives described above for the albumin solution, which are compatible with the carbodiimide, may be used.

In one embodiment, the invention provides a kit comprising a first vessel containing an aqueous solution comprising albumin, gelatin, or albumin and gelatin, and at least one of a polyamine and/or a polycarboxylate; a second vessel containing an undissolved water-soluble carbodiimide; and a third vessel, the contents of which comprises water.

In another embodiment, the invention provides a kit comprising a first vessel containing an aqueous solution comprising albumin, gelatin, or albumin and gelatin; a second vessel containing an undissolved water-soluble carbodiimide; a third vessel, the contents of which comprises water; and a fourth vessel containing a polyamine as a neat liquid or an aqueous solution comprising at least one of a polyamine and/or a polycarboxylate.

In another embodiment, the invention provides a kit comprising a first vessel containing an aqueous solution comprising albumin, gelatin, or albumin and gelatin; a second vessel containing an undissolved water-soluble carbodiimide; and a third vessel, the contents of which comprises water and at least one of a polyamine and/or a polycarboxylate.

The vessels used to contain the various components may be any suitable vessel, such as a vial or a syringe barrel. For use on living tissue, it is preferred that all the vessels and their contents be sterilized.

Method of Application:

At the time of use, the undissolved water-soluble carbodiimide is hydrated with the required amount of water to form an aqueous solution comprising the water-soluble carbodiimide at a concentration of about 5% to about 50% by weight. This may be done by adding the water to the vessel comprising the undissolved water-soluble carbodiimide using any suitable device, such as a pipet or a syringe. Alternatively, the vessel comprising the water and the vessel comprising the undissolved water-soluble carbodiimide may be separated by a frangible barrier that can be ruptured by pressure, for example by squeezing, bending, or using a plunger. After the barrier is ruptured, the two components may be mixed by shaking to form the aqueous solution comprising the water-soluble carbodiimide at the desired concentration.

A coating may be formed on an anatomical site on tissue of a living organism by forming on the site an aqueous mixture comprising albumin, gelatin, or albumin and gelatin; a water-soluble carbodiimide; and a polyamine and/or a polycarboxylate of the invention, and allowing the aqueous mixture to cure. In the aqueous mixture, the water-soluble carbodiimide concentration is about 1% to about 10% by weight, preferably about 2% to about 4% by weight; the concentration of the polyamine, if present, is about 0.4% to about 20% by weight; and the concentration of the polycarboxylate, if present, is about 0.4% to about 5% by weight. If both the polyamine and the polycarboxylate are present in the aqueous mixture, then the concentration of the polyamine is about 0.4% to about 20% by weight, and the concentration of the polycarboxylate is about 0.4% to about 5% by weight. The concentration of albumin in the aqueous mixture is about 20% to about 36% by weight when the mixture contains albumin, but not gelatin. The concentration of gelatin in the aqueous mixture is about 12% to about 32% by weight when the mixture contains gelatin, but not albumin. When both albumin and gelatin are present in the aqueous mixture, the total protein concentration is about 12% to about 36% by weight. Preferably the concentrations of albumin and gelatin in the aqueous mixture containing both proteins is about 1% to about 35% and about 1% to about 31%, respectively.

The aqueous mixture comprising the various components described above may be formed on the site in any number of ways. For example, the aqueous protein solution and the aqueous solution comprising the water-soluble carbodiimide, at least one of which further comprises a polyamine and/or a polycarboxylate, may be applied to an anatomical site on tissue of a living organism to form the aqueous mixture. Once both solutions are applied to the site, they crosslink to form the coating which is a hydrogel, a process referred to herein as curing, typically in about 1 to about 5 minutes. Because the activated carboxyl groups on the albumin or gelatin may also covalently bind to amine groups on the tissue, the protein-based tissue adhesive of the invention is capable of covalently binding to tissue, thereby increasing its adhesive strength.

In one embodiment, the two aqueous solutions are applied to the site sequentially using any suitable means including, but not limited to, spraying, brushing with a cotton swab or brush, or extrusion using a pipet, or a syringe. The solutions may be applied in any order. Then, the solutions are mixed on the site using any suitable device, such as a cotton swab, a spatula, or the tip of the pipet or syringe.

In another embodiment, the two aqueous solutions are mixed manually before application to the site. The resulting mixture is then applied to the site before it completely cures using a suitable applicator, as described above.

In another embodiment, the two aqueous solutions are applied to the site using a double-barrel syringe. One barrel of the syringe contains the protein solution and the second barrel contains the aqueous solution comprising the water-soluble carbodiimide. The aqueous solution comprising the water-soluble carbodiimide may be added to the syringe barrel, or formed within the syringe barrel in any number of ways. For example, the water and the undissolved water-soluble carbodiimide may be contained in separate vials. The desired amount of water is added to the vial containing the undissolved water-soluble carbodiimide to form the aqueous solution comprising the water-soluble carbodiimide, which is then introduced into the syringe barrel. Alternatively, the undissolved water-soluble carbodiimide may be contained in the syringe barrel and the water may be contained in a third vessel, such as a sealed vial. The desired amount of water is added to the syringe barrel containing the undissolved water-soluble carbodiimide to form the aqueous solution comprising the water-soluble carbodiimide. Alternatively, the syringe barrel may contain the water and a frangible capsule containing the undissolved water-soluble carbodiimide. The capsule is ruptured by depressing the plunger, allowing the undissolved water-soluble carbodiimide to be mixed with the water to form the aqueous solution comprising the water-soluble carbodiimide.

The use of a double-barrel syringe permits the two aqueous solutions to be applied to the site simultaneously. Suitable double-barrel syringe applicators are known in the art. For example, Redl describes several suitable applicators for use in the invention in U.S. Pat. No. 6,620,125, (particularly FIGS. 1, 5, and 6, which are described in Columns 4, line 10 through column 6, line 47) which is incorporated herein by reference. Additionally, the double barrel syringe may contain a motionless mixer, such as that available from ConProtec, Inc. (Salem, N.H.), at the tip to effect mixing of the two aqueous solutions prior to application.

In another embodiment wherein the polyamine and/or the polycarboxylate is contained in a separate third solution, the three solutions are applied to the anatomical site in any order using any of the methods described above to form the aqueous mixture. In this embodiment, the double-barrel syringe may be modified to have three barrels, one for each of the solutions.

In another embodiment, the tissue adhesive of the invention is used to bond at least two anatomical sites together. In this embodiment, an aqueous mixture comprising albumin, gelatin, or albumin and gelatin; a water-soluble carbodiimide; and a polyamine and/or a polycarboxylate of the invention is formed in contact with at least two anatomical sites. The aqueous mixture in contact with at least two anatomical sites may be formed in various ways. For example, the protein solution may be applied to at least one anatomical site, and the aqueous solution comprising the water-soluble carbodiimide may be applied to at least one of either the same site or one other site. At least one of the protein solution or the water-soluble carbodiimide solution further comprises a polyamine and/or a polycarboxylate. The two or more sites are contacted and held together manually or using some other means, such as a surgical clamp, for a time sufficient for the mixture to cure, typically about 1 to about 5 minutes. Alternatively, a mixture of the two aqueous solutions, either premixed manually or using a double-barrel syringe applicator, is applied to at least one of the anatomical sites to be bonded. The two or more sites are contacted and held together manually or using some other means, such as a surgical clamp, for a time sufficient for the mixture to cure.

In another embodiment wherein the polyamine and/or polycarboxylate is contained in a separate third solution and is used along with the protein solution and the aqueous solution comprising the water-soluble carbodiimide to bond at least two anatomical sites together, each of the three solutions is applied to at least one anatomical site in any order. The solutions may be applied to the same site or to different sites. Alternatively, the three solutions are premixed using any of the methods described above, and the resulting mixture is applied to at least one of the anatomical sites to be bonded before the mixture completely cures. The two or more sites are then contacted and held together manually or using some other means, such as a surgical clamp, for a time sufficient for the mixture to cure Medical and Veterinary Applications:

The tissue adhesive of the invention has many potential medical and veterinary applications, including, but not limited to, topical wound closure, surgical procedures, such as intestinal anastomosis, vascular anastomosis, and ophthalmic procedures; drug delivery, anti-adhesive applications, and as a bulking agent to treat urinary incontinence. For these uses, procedures involving the application of two aqueous solutions, the protein solution and the aqueous solution comprising the water-soluble carbodiimide, at least one of which further comprises a polyamine and/or a polycarboxylate, are described below. The application of three solutions, wherein the third solution comprises a polyamine and/or a polycarboxylate, may also be used for these purposes using the procedures described above.

The tissue adhesive of the invention may be used for treatment of topical wounds, including but not limited to, minor cuts, scrapes, irritations, abrasions, lacerations, burns, sores, and surgical wounds. For topical wound closure, the protein solution and the aqueous solution comprising the water-soluble carbodiimide are applied to the wound using the methods described above, and the mixture is allowed to cure.

The tissue adhesive of the invention may also be used in surgical procedures, including but not limited to, intestinal anastomosis, vascular anastomosis, and ophthalmic procedures, such as sealing corneal cataract incisions.

Intestinal anastomosis is a surgical procedure that is well known to skilled surgeons. The procedure, which involves joining two segments of the intestine together after a resection, is described by Sweeney et al. (*Surgery* 131:185-189 (2002)). The two segments of the intestine are joined together using sutures or staples. A problem encountered with this procedure is leakage around the sutures or staples. Leakage rates of 5-8% have been reported (Bruce et al. *Br. J. Surg.* 88:1157-1168 (2001)). The tissue adhesive of the invention may be used to supplement the sutures or staples used in intestinal anastomoses, providing a better seal that reduces leakage. In this application, the protein solution and the aqueous solution comprising the water-soluble carbodiimide are applied to the intestine around the sutures or staples, using the methods described above, and the mixture is allowed to cure.

Additionally, the tissue adhesive of the invention may be used in vascular anastomosis procedures. This procedure is similar to intestinal anastomosis, described above, and is used for vascular grafts. The two segments of the blood vessel are joined together using sutures or staples. The tissue adhesive of the invention may be used to supplement the sutures or staples, providing a better seal that reduces leakage. In this application, the protein solution and the aqueous solution comprising the water-soluble carbodiimide are applied to the blood vessel around the sutures or staples, using the methods described above and the mixture is allowed to cure.

Temporal clear corneal incisions and scleral tunnel incisions are used during cataract surgery. These procedures are well known to the skilled cataract surgeon. Although these incisions can be sealed with sutures, many surgeons prefer sutureless, self-sealing incisions. However, problems arise with leakage through the sutureless incisions, causing endophthalmitis (Sarayba et al. Amer. *J. Opthamol.* 138:206-210 (2004), and Kim et al. *J. Cataract Refract. Surg.* 21:320-325 (1995)). The tissue adhesive of the invention may be used to seal both clear corneal incisions and scleral tunnel incisions to prevent leakage. In this application, the protein solution and the aqueous solution comprising the water-soluble carbodiimide are applied to the site of the incision in the eye, using the methods described above, and the mixture is allowed to cure. Additionally, the two aqueous solutions may be coated on the sides of the scalpel blade used to make the incision, one solution on each side of the blade, to apply them to the site when the site is ready for closure.

The tissue adhesive of the invention may also be used to prevent adhesions between adjacent anatomical sites following surgery or injury to internal organs. The protein solution and the aqueous solution comprising the water-soluble carbodiimide are applied to one anatomical site using the methods described above. The first site is prevented from contacting any adjacent site manually or using some other means, such as a surgical clamp, until the mixture cures, typically about 1 to about 5 minutes. After curing, the hydrogel is no longer adhesive, and serves as a barrier preventing adhesions of adjacent sites.

The tissue adhesive of the invention may also be used for drug delivery to a selected anatomical site. In this application, one of the aqueous solutions further comprises a pharmaceutical drug or therapeutic agent. Alternatively, the pharmaceutical drug or therapeutic agent may be contained in a separate aqueous solution. Suitable pharmaceutical drugs and therapeutic agents are well known in the art. An extensive list is given by Kabonov et al. in U.S. Pat. No. 6,696,089, which is incorporated herein by reference (in particular, columns 16 to 18). Examples include, but are not limited to, antibacterial agents, antiviral agents, antifungal agents, anti-cancer agents, vaccines, radiolabels, anti-inflammatories, anti-glaucomic agents, local anesthetics, anti-neoplastic agents, antibodies, hormones, and the like. In this application, the protein solution and the aqueous solution comprising the water-soluble carbodiimide, at least one of which further comprises the pharmaceutical drug or therapeutic agent of interest, are applied to the desired anatomical site using the methods described above. After the hydrogel cures, the drug or therapeutic agent is released to the desired anatomical site. The rate of release depends on the crosslink density of the hydrogel, which can be controlled by the extent of crosslinking, which in turn is determined by the concentrations of the water-soluble carbodiimide, the albumin and/or gelatin, and the polyamine and/or polycarboxylate used. The concentration of reagents needed to obtain the proper rate of drug release for any particular application can be readily determined by one skilled in the art using routine experimentation.

The tissue adhesive of the invention may also be used as a bulking agent to treat urinary incontinence, particularly, female stress urinary incontinence. Stress urinary incontinence is the loss of urine from the bladder caused by pressure occurring during exercise, coughing, sneezing, etc. One cause of this problem is the weakening of the urethral sphincter, a ring-shaped muscle at the base of the bladder that controls the flow of urine. One remedy for this condition is to use a bulking agent to provide physical support to the urethral sphincter. In this application, the protein solution and the aqueous solution comprising the water-soluble carbodiimide are applied to the tissue surrounding the sphincter, using the methods described above, preferably a mixture of the two aqueous solutions is injected using a standard cytoscope. The mixture cures into a firm, but pliable hydrogel. The increased bulk at the injection site provides the sphincter muscles with additional capability to control urine flow.

Additionally, the tissue adhesive of the invention may be used for other medical applications. These applications include, but are not limited to, an adhesive to hold an implant in place; an adhesive used on tissue to block air, moisture, fluid or microbial migration; and an adhesive to replace or supplement sutures or staples in other surgical procedures, such as cholecystectomy, ostomy port, appendectomy, bariatrics, retinal reattachment, Cesarean closure, abdominal hysterectomy, and the closure of trauma punctures, and ruptured membranes.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "mL" means milliliter(s), "L" means liter(s), "µL" means microliter(s), "cm" means centimeter(s), "mm" means millimeter(s), "µm" means micrometer(s), "mol" means mole(s), "mmol" means millimole(s), "g" means gram(s), "mg" means milligram(s), "MW" means molecular weight, "$M_W$" means weight-average molecular weight, "$M_V$" means viscosity-average molecular weight, "M" means molar concentration, "wt %" means percent by weight, "v/v" means volume to volume ratio, "rpm" means revolutions per minute, "kGy" means kilogray, "psi" means pounds per square inch, "kPa" means kilopascals, "$^1$H NMR" means proton nuclear magnetic resonance spectroscopy, and a reference to "Aldrich" or a reference to "Sigma" means the said chemical or ingredient was obtained from Sigma-Aldrich, St. Louis, Mo.

General Methods:

The concentrations of the albumin and/or gelatin, the water-soluble carbodiimide, and the polyamine and/or polycarboxylate given in the Tables in all the following Examples are the final concentrations in the aqueous mixture resulting from mixing the components.

Reagents:

The following reagents were used in the Examples:

8-arm poly(ethylene glycol) octamine (8PEGA), MW=10,000, Nektar Transforming Therapeutics (Huntsville, Ala.), 0J2V0L18;

Bovine serum albumin (BSA), Sigma A-7906;

Bovine serum albumin (Sigma A-7906) dissolved in deionized water, adjusted to pH 4.4 by addition of 1 M HCl, and lyophilized (mBSA);

Carboxymethyl cellulose (CMC), sodium salt, ultra-low viscosity, Aldrich 360384;

1-ethyl-3-(3-dimethylamino)propylcarbodiimide hydrochloride (EDC), Advanced ChemTech Inc. (Louisville, Ky.), RC8102;

Gelatin, bovine, 75 bloom, Sigma G6650;

Gelatin, fish, MW 60,000, Sigma G7041;

Poly(acrylic acid) (PAA), sodium salt, $M_V$ 15,000, Aldrich 416037;

Poly(allylamine hydrochloride) (PAH-15K), $M_W$ 15,000, Aldrich 283215;

Poly(ethyleneimine) (PEI-25K), $M_W$=25,000, Aldrich 408727;

Poly(ethyleneimine) (PEI-800), $M_W$=800, Aldrich 408719;

Poly(ethyleneimine) (PEI-HCl-25K), $M_W$=25,000, Aldrich 408727, adjusted to pH 5 to 6 with hydrochloric acid and lyophilized;

Poly(ethyleneimine) (PEI-HCl-800), $M_W$=800, Aldrich 408719, adjusted to pH 5 to 6 with hydrochloric acid and lyophilized;

Poly-L-lysine hydrochloride (pLysHCl), MW=15,000-30,000, Sigma P-2658.

Preparation of 3-Aminopropyl Dextran (AP-Dextran)

To 2 g of dextran ($M_W$ of approximately 10,000, Sigma D9260) in 10 mL of water, was added 2 mL of 1 N NaOH, followed by 0.685 mL of acrylonitrile. After the reaction had stirred for 2 h at room temperature, it was neutralized by adding dilute hydrochloric acid. The solvent was removed by lyophilization to give cyanoethyl dextran (degree of substitution 0.37 by $^1$H NMR).

The intermediate cyanoethyl dextran was reduced using sodium borohydride and cobalt chloride according to Verraest, et al. (Starch/Stärke 48:191-195 (1996)). The reaction mixture was filtered through a pad of Celite® 545 (Spectrum Laboratory Products, Gardena, Calif.; C1196) and stripped of solvent by rotary evaporation. The residue was dissolved in a small amount of water, dialyzed against deionized water using a dialysis membrane having a molecular weight cut-off of 2,000 Daltons, and recovered by lyophilization to give 3-aminopropyl dextran (degree of substitution 0.32 by $^1$H NMR).

Examples 1-9

Lap Shear Strength

The purpose of these Examples was to demonstrate the beneficial effect of auxiliary polyamine or polycarboxylate on the lap shear strength of various protein-based adhesives when applied to collagen film.

A total volume of 50 μL of adhesive components, 40 μL of protein solution (with auxiliary polyamine or polycarboxylate) and 10 μL of EDC solution, were delivered by micropipettor and spread over a 1-cm$^2$ area of contact between two 1 cm-wide strips of damp collagen film (from washed sausage casing, obtained from The Sausage Source, Hillsboro, N.H.). The strip ends were rubbed together to mix the components and then cured under a 25 g/cm$^2$ weight for 30 min. A cloth loop was attached to one end of the assembly and lap shear determined by lifting weights of increasing mass, typically 100, 200 or 250, 350 or 375, 500, 650, 800 and 1000 g. To lift 500 and 1000-g weights without the collagen itself breaking, the collagen strips had to be doubled over. The mass at which an adhesive failed was noted. Solutions that contained mammalian gelatin were generally kept at 50° C. prior to application to prevent them from gelling prematurely. The results are given in Table 1.

TABLE 1

Lap Shear Strengths of Adhesives on Collagen Film

| Example | Protein (wt %) | Poly-amine (wt %) | Poly-carboxylate (wt %) | wt % EDC | Lap shear failure, g/cm$^2$ |
|---|---|---|---|---|---|
| 1 | bovine gelatin (20) | — | CMC (1) | 4 | 650 |
| 2, Comparative | fish gelatin (28) | — | — | 4 | 375 |
| 3, Comparative | fish gelatin (28) | — | PAA (1) | 4 | 250 |
| 4, Comparative | fish gelatin (28) | — | PAA (2) | 4 | 100 |
| 5, Comparative | fish gelatin (20) bovine gelatin (8) | — | — | 6 | 350 |
| 6 | fish gelatin (20) bovine gelatin (8) | — | CMC (1.7) | 6 | 500 |
| 7, Comparative | BSA (28) | — | — | 4 | 100 |
| 8, Comparative | BSA (28) | — | — | 6 | 200 |
| 9, Comparative | BSA (28) | PEI-HCl-800 (8) | — | 8 | 250 |

These Examples demonstrate that the addition of an auxiliary polycarboxylate of the invention enhances the strength of protein-based adhesives, as measured by the lap shear strength. The addition of polyethyleneimine at a higher concentration and with a higher EDC concentration did not result in a large increase in lap shear strength. The addition of poly(acrylic acid) (PAA), a polycarboxylate accessory molecule described by Tammishetti et al. (WO 99/66964), resulted in a decrease in lap shear strength.

Examples 10-20

In Vitro Pig Uterine Horn Burst Strength

The purpose of these Examples was to demonstrate the effective seal formed by various protein-based adhesives when applied as a sealant to an incision made in a uterine horn of a pig. Internal pressure within the lumen of the uterine horn is approximately 1 psi (6.895 kPa).

A 5 to 6-mm incision was made using a #15 surgical blade in a 6 to 8-cm section of clean, fresh pig uterine horn (obtained from a local abattoir). The wound was sealed by applying 40 μL of protein solution (with auxiliary polyamine) and 10 μL of EDC solution simultaneously by micropipettor and mixing with the pipettor tips or a small, plastic spatula. After the adhesive had been allowed to cure (typically 2 to 5 min), one end of the section of uterine horn was secured to a metal nipple with a nylon cable tie, and the other end was clamped shut. The metal nipple was connected by plastic tubing to a syringe pump (Model No. 22, Harvard Apparatus, Holliston, Mass.) equipped with a pressure meter. The section of uterine horn was submerged in a beaker of water, and dyed water was pumped by the syringe pump into the uterine horn section at 11 mL/h. The pressure at which the sealed wound leaked was noted. The results are given in Table 2.

TABLE 2

In Vitro Burst Pressures of Adhesives Used to Seal an Incision in Pig Uterine Horn

| Example | Protein (wt %) | Polyamine (wt %) | EDC wt % | Burst Pressure, psi (kPa) |
|---|---|---|---|---|
| 10 | mBSA (28) | 8PEGA (8) | 2 | 1.82 (12.5) |
| 11 | mBSA (28) | 8PEGA (8) | 4 | 3.29 (22.7) |
| 12 | mBSA (28) | 8PEGA (8) | 5 | 3.72 (25.6) |
| 13 | mBSA (28) | 8PEGA (8) | 6 | 4.36 (30.1) |
| 14 | mBSA (28) | 8PEGA (4) | 2 | 1.86 (12.8) |
| 15 | mBSA (28) | 8PEGA (5.6) | 4 | 3.20 (22.1) |
| 16 | mBSA (28) | 8PEGA (4) | 5 | 3.65 (25.2) |
| 17 | mBSA (28) | 8PEGA (4.8) | 5 | 2.26 (15.6) |
| 18 | mBSA (28) | 8PEGA (5.6) | 5 | 2.13 (14.7) |
| 19, Comparative | BSA (29) | PEI-HCl-800 (8) | 8.3 | 0.52 (3.58) |
| 20, Comparative | BSA (29) | PEI-HCl-25K (8) | 8.3 | 0.15 (1.03) |

These Examples demonstrate that protein-based adhesives comprising an auxiliary polyamine of the invention are effective in sealing an incision in pig intestine and result in high burst pressures. Protein-based adhesives containing polyethyleneimine had significantly lower burst pressures with higher concentrations of EDC. This result demonstrates that the polyamines of the invention enable the use of lower EDC concentrations to produce an adhesive with good adhesive strength.

Examples 21-24

In Vitro Degradation of Protein-Based Tissue Adhesives

The purpose of these Examples was to demonstrate the in vitro mechanical stability of the protein-based adhesives of the invention.

Thin films of adhesives weighing 0.20 to 0.30 g were prepared by combining an aqueous solution of mBSA and 8PEGA and an aqueous solution of EDC in a 4:1 v/v ratio on a glass plate and mixing with a small spatula. After the films had cured, each was detached and placed in a jar containing phosphate-buffered saline, pH 7.4, and the jars were incubated at 37° C. with orbital shaking at 80 rpm. The samples were monitored for degradation by visual inspection and weight gain or loss. The results are summarized in Table 3.

TABLE 3

In Vitro Degradation of Tissue Adhesives

| Example | wt % mBSA | Poly-amine (wt %) | wt % EDC | Appearance 2 days | Appearance 15 days | % Weight gain/loss 2 days | % Weight gain/loss 15 days |
|---|---|---|---|---|---|---|---|
| 21 | 28 | 8PEGA (4) | 2 | intact | fragile, friable | +46 | NA |
| 22 | 28 | 8PEGA (8) | 2 | intact | intact | +24 | +25 |
| 23 | 28 | 8PEGA (8) | 3 | intact | intact | +32 | +32 |
| 24 | 28 | 8PEGA (8) | 10 | intact | intact | +14 | +14 |

These Examples demonstrate the mechanical stability of the protein-based adhesives of the invention.

Examples 25-35

In Vitro Extract Cytotoxicity

The purpose of these Examples was to demonstrate the safety of various protein-based adhesives comprising albumin, a polyamine, and EDC. Tests were done using Chinese hamster ovary (CHO-K1) cell cultures according to ISO10993-5:1999. The CHO-K1 cells were obtained from the American Type Culture Collection (ATCC), Manassas, Va., and were grown in F12-K medium supplemented with 10% fetal bovine serum.

The cytotoxicities of the crosslinked hydrogels were measured by extracting 100 mg of crosslinked hydrogel with 1 mL of culture medium for 24 h at 37° C. Extracts (100 µL) were added to CHO-K1 cells that had been plated out at 50,000 cells per well in a culture plate, incubated in 100 µL of culture medium for 24 h, and decanted of medium. After incubation of CHO-K1 cells with the adhesive extracts for 18 h at 37° C., cell viability was determined by a colorimetric assay of mitochondrial dehydrogenase-catalyzed reduction of MTT (Sigma TOX-1®; Sgouras, et al. *Journal of Materials Science Materials in Medicine* 1:61-68 (1990)) and an adenylate kinase-based luminescence assay of ATP (ToxiLight®; Crouch, et al. *Journal of Immunological Methods* 160:81-88 (1993)). The results are given in Table 4.

TABLE 4

In Vitro Cytotoxicities of Hydrogel Extracts Made at 100 mg/mL

| Example | Adhesive Composition, wt %[a] polyamine (wt %) | EDC | CHO-K1 cell viability, % |
|---|---|---|---|
| 25 | AP-dextran (8) | 4 | 96 |
| 26 | 8PEGA (8) | 4 | 79 |
| 27, Comparative | PAH-15K (8) | 4 | 61 |
| 28, Comparative | pLysHCl (8) | 4 | 57 |
| 29, Comparative | PEI-25K (8) | 4 | 6 |
| 30 | 8PEGA (5.6) | 4 | 83 |
| 31, Comparative | PAH-15K (5.6) | 4 | 74 |
| 32, Comparative | pLysHCl (5.6) | 4 | 48 |
| 33 | 8PEGA (4) | 4 | 72 |
| 34 | 8PEGA (8) | 2 | 98 |
| 35, Comparative | pLysHCl (8) | 2 | <7 |

[a]All adhesives contained 28 wt % mBSA.

These Examples demonstrate that the protein-based adhesives comprising the polyamines of the invention are less toxic than adhesives made with the polyamines that were previously reported (Tammishetti et al. WO 99/66964), or other similar polyamines, such as polyethyleneimine.

Examples 36-39

In Vitro Polyamine Cytotoxicity

The purpose of these Examples was to demonstrate the inherent cytotoxicities of various polyamines that might be used as components of the protein-based adhesives of the present invention. Tests were done using Chinese hamster ovary (CHO-K1) cell cultures according to ISO10993-5: 1999. The CHO-K1 cells were obtained from the American Type Culture Collection (ATCC), Manassas, Va., and were grown in F12-K medium supplemented with 10% fetal bovine serum.

Cytotoxicities of polyamines were determined as described Examples 25-35, except that 100 µL of a 10 wt % aqueous solution of each polyamine was mixed with 1 mL of culture medium, incubated for 24 h at 37° C., serially diluted, and then 100 µL of each of these solutions was added to the CHO-K1 cells. The CHO-K1 cells had previously been plated out at 50,000 cells per well in a culture plate, incubated in 100 µL of culture medium for 24 h, and decanted of medium. After incubation of CHO-K1 cells with the serially diluted polyamine solutions for 18 h at 37° C., cell viability was determined by a colorimetric assay of mitochondrial dehydrogenase-catalyzed reduction of MTT (Sigma TOX-1®; Sgouras, et al. *Journal of Materials Science: Materials in Medicine* 1:61-68 (1990)) and an adenylate kinase-based luminescence assay of ATP (ToxiLight®; Crouch, et al. *Journal of Immunological Methods* 160:81-88 (1993)). The results are summarized in Table 5.

TABLE 5

Cytotoxicities of Polyamines

| | | CHO-K1 Cell Viability | | | | | |
|---|---|---|---|---|---|---|---|
| Example | Polyamine | 50 mg/mL | 10 mg/mL | 5 mg/mL | 1 mg/mL | 0.5 mg/mL | 0.05 mg/mL |
| 36 | 8PEGA | 100 | — | 100 | — | 100 | 100 |
| 37, Comparative | pLysHCl | — | 0.8 | — | 94 | — | — |
| 38, Comparative | PEI-25K | — | — | — | — | 7 | 86 |
| 39, Comparative | PEI-800 | — | — | — | — | 82 | 89 |

These Examples demonstrate that polyamines of the invention are less toxic than the polyamines that were previously reported (Tammishetti et al. WO 99/66964), or other similar polyamines such as polyethyleneimine.

Examples 40-47

In Vitro Contact Cytotoxicity Testing

The purpose of these Examples was to demonstrate the safety of various protein-based adhesives comprising NIH3T3 mouse fibroblasts in vitro.

The testing was done using NIH3T3 mouse fibroblast cell cultures according to ISO10993-5:1999. The NIH3T3 mouse fibroblast cells were obtained from ATCC and were grown in Dulbecco's modified essential medium (DMEM), supplemented with 10% fetal calf serum.

Hydrogel samples were prepared by applying 80 μL of protein/polyamine solution and 20 μL of EDC solution simultaneously by micropipettor to the bottom of a well of a 24-well polystyrene culture plate and mixing with a small, plastic spatula. Each well had about ¼ of its bottom covered by the hydrogel. Culture plates were then sterilized under UV light, and each well was seeded with 50,000-100,000 NIH3T3 cells. The cells were observed after 24 and 48 h for growth and spreading.

The results are summarized in Table 6. A score of "pass" indicates that the cells grew and spread to normal confluency, coating the bottom of the well and coming in contact with but not overgrowing the hydrogel. This result demonstrates a lack of cytotoxicity of the hydrogel and a lack of adhesion of cell cultures to the hydrogel. A score of "fail" indicates that the cells failed to grow normally, typically remaining spherical and often detaching from the polystyrene surface.

TABLE 6

In Vitro Contact Cytotoxicities of
Hydrogels with NIH3T3 Fibroblasts

| | Adhesive Composition, wt %[a] | | | | |
|---|---|---|---|---|---|
| Example | 8PEGA | pLysHCl | PAH-15K | EDC | Score |
| 40 | 4 | — | — | 2 | pass |
| 41, Comparative | — | 4 | — | 2 | fail |
| 42 | 8 | — | — | 2 | pass |
| 43, Comparative | — | 8 | — | 2 | fail |
| 44, Comparative | — | — | 8 | 2 | fail |
| 45 | 5.6 | — | — | 4 | pass |
| 46, Comparative | — | 5.6 | — | 4 | fail |
| 47, Comparative | — | — | 5.6 | 4 | fail |

[a]All adhesives contained 28 wt % mBSA.

These Examples demonstrate that the protein-based adhesives comprising the polyamines of the invention are less toxic than adhesives made with the polyamines that were previously reported (Tammishetti et al. WO 99/66964).

Examples 48-53

In Vitro Testing of Inflammatory Potential

The purpose of these Examples was to demonstrate the noninflammatory response produced by various protein-based adhesives comprising albumin, a polyamine, and EDC when in contact with J774 macrophages in vitro.

The testing was done using J774 macrophage cultures according to ISO10993-5:1999. The J774 macrophage cells were obtained from ATCC and were grown in DMEM supplemented with 10% fetal bovine serum.

Hydrogel samples were prepared by applying 80 μL of protein/polyamine solution and 20 μL of EDC solution simultaneously by micropipettor to the bottom of a well of a 24-well polystyrene culture plate and mixing with a small, plastic spatula. Each well had about ¼ of its bottom covered by the hydrogel. Culture plates were then sterilized under UV light, and each well was seeded with J774 mouse peritoneal macrophage cells. After 48 h, the cell cultures were analyzed for release of TNF-α, an indicator of inflammatory response, using an ELISA assay (Lara, et al. *Journal of Dental Research* 82:460-465 (2003)). Macrophage cells were incubated in untreated wells and in wells containing bacterial lipopolysaccharide (LPS) to generate negative and positive controls, respectively. The results are given in Table 7. A score of "pass" indicates that the TNF-α titer of a sample was similar to that of the negative control.

TABLE 7

Contact Cytotoxicities of Hydrogels with 3T3 Fibroblasts

| Example | Adhesive Composition, wt %[a] | | | Score |
| --- | --- | --- | --- | --- |
| | 8PEGA | pLysHCl | EDC | |
| 48 | 4 | — | 2 | pass |
| 49 | 8 | — | 2 | fail |
| 50, Comparative | — | 4 | 2 | pass |
| 51 | 4 | — | 3 | pass |
| 52 | 8 | — | 3 | fail |
| 53, Comparative | — | 4 | 3 | fail |

[a] All adhesives contained 28 wt % mBSA.

These Examples demonstrate that the protein-based adhesives comprising the polyamines of the invention are less toxic than adhesives made with the polyamines that were previously reported (Tammishetti et al. WO 99/66964).

Example 54

Sterilization of Tissue Adhesive Components and Delivery Devices

The purpose of this Example was to demonstrate the sterilization of aqueous solutions comprising albumin and a polyamine, undissolved EDC, and the components of a delivery device.

Aqueous solutions comprising mBSA (35 wt %) and 8PEGA (5, 6, and 7 wt %) were loaded into glass vials, which were then sealed with serum caps. Dry EDC and sterile water were also loaded separately into glass vials, which were then sealed with serum caps. All of these components, along with plastic disposable syringes, disposable syringe needles, plastic "Y" mixing connectors (Micromedics, Inc., St. Paul, Minn.), plastic collars and plunger base plates to allow simultaneous application of components from two syringes, and plastic applicator tips, were sterilized by gamma irradiation under a flux of 25 kGy ($2.5 \times 10^6$ rad). The solutions may also be contained in sealed, disposable syringes during irradiation.

The sterilized solutions of albumin and 8PEGA were tested for gelation, using the sterilized EDC and water to prepare a solution at the time of testing. Hydrogels prepared from these components were also tested for in vitro burst pressure of sealed incisions in pig intestine, in vitro extract cytotoxicity, and in vitro contact toxicity, using the methods described in the previous Examples. Hydrogel components were dispensed using the sterilized syringes, "Y" mixing connector, collar, plunger base plate and applicator tips or using micropipettors with sterile tips. The mechanical and cytotoxicological properties of the sterilized hydrogel components were very similar to those of the unsterilized components.

Examples 55-57

In Vivo Biocompatibility Testing

The purpose of these Examples was to demonstrate the in vivo safety of protein-based adhesives comprising albumin, a polyamine, and EDC by "painting" the adhesive material onto the small intestine of living rabbits.

White New Zealand rabbits (1 year old, approximately 4 kg in weight) were fasted overnight. Prior to surgery, the animals were treated with buprenorphine, then anaesthetized with a mixture of ketamine and xylazine. A standard laparotomy procedure was performed to isolate a section of the duodenum of the small intestine. To aid in locating the hydrogel patch at the time of necropsy, a single stitch of blue-dyed polypropylene suture material (Prolene®, Ethicon) was placed at the duodenum, in the outer layer of intestinal tissue, about 10 cm distal from the stomach. Using micropipettors, about 120 μL of a solution comprising 35 wt % mBSA and 7 wt % 8PEGA and 30 μL of a solution comprising 10, 15 or 20 wt % EDC were applied simultaneously to the duodenum, about 12 cm distal from the stomach, using the micropipettor tips to stir the mixture. Each hydrogel composition was placed on the duodenum of five different rabbits. The patch of hydrogel on the surface of the duodenum was about 1 cm×2 cm and covered about 90% of the circumference of the intestine, leaving the mesentery uncovered. After the hydrogel had cured for 2 min, the peritoneum and abdomen were closed in layers using standard surgical procedure.

At necropsy 3 days later, the hydrogel was found intact with good adhesion at each site of application. Using a scoring system consistent with the ISO intracutaneous reactivity test (ISO 10993-12), no edema was observed (score 0). Erythema scores are shown in Table 8. There were no fibrous adhesions or attachments to the site of application or adjacent tissue.

TABLE 8

Erythema Observed After In Vivo Application of Hydrogel to Rabbit Intestine

| Example | final [EDC], wt % | Erythema score (ISO 10993-12) | | | | |
| --- | --- | --- | --- | --- | --- | --- |
| | | rabbit 1 | rabbit 2 | rabbit 3 | rabbit 4 | rabbit 5 |
| 55 | 4 | 2 | 2 | 2 | 3 | 2 |
| 56 | 3 | 2 | 1 | 2 | 2 | 3 |
| 57 | 2 | 1 | 2 | 2 | 2 | 4 |

These Examples demonstrate that the erythema caused by the protein-based adhesive of the invention was generally mild (average score of 2).

What is claimed is:

1. A cured composition obtained from an aqueous mixture comprising: (a) at least one of albumin or gelatin; (b) a water-soluble carbodiimide; and (c) at least one water-dispersible multi-arm polyether amine, the total water-dispersible multi-arm polyether amine concentration being in the range of about 0.4% to about 20% by weight; and, (d) optionally, at least one polycarboxylate selected from the group consisting of carboxymethyl cellulose, carboxymethyl dextran, and carboxymethyl starch; wherein the aqueous mixture is allowed to cure; provided that: (i) if the aqueous mixture comprises albumin, but not gelatin, then the concentration of albumin in the aqueous mixture is about 20% to about 36% by weight; (ii) if the aqueous mixture comprises gelatin, but not albumin, then the concentration of gelatin in the aqueous mixture is about 12% to about 32% by weight; (iii) if the aqueous mixture comprises a mixture of albumin and gelatin, then the total concentration of albumin and gelatin combined is about 12% to about 36% by weight; (iv) the concentration of the water-soluble carbodiimide in the aqueous mixture is about 1% to about 10% by weight; (v) if the aqueous mixture comprises the polyether amine, but not the polycarboxylate, then the concentration of the polyether amine in the aqueous mixture is about 0.4% to about 20% by weight; (vi) if the aqueous mixture comprises both the polyether amine and the polycarboxylate, then the concentration of the polyether amine in the aqueous mixture is about 0.4% to about 20% by weight and the concentration of the polycarboxylate is about 0.4% to about 5% by weight.

2. The composition according to claim 1 wherein the albumin is selected from the group consisting of a mammalian serum albumin, an egg albumin, and mixtures thereof.

3. The composition according to claim 2 wherein the mammalian serum albumin is selected from the group consisting of bovine serum albumin, ovine serum albumin, porcine serum albumin, human serum albumin, equine serum albumin, lapine serum albumin, rat serum albumin, murine serum albumin, and mixtures thereof.

4. The composition according to claim 2 wherein the egg albumin is chicken egg albumin.

5. The composition according to claim 1 wherein said at least one albumin or gelatin, said water-soluble carbodiimide, said at least one polyamine, and said at least one polycarboxylate are sterilized.

6. The composition according to claim 1 wherein the aqueous mixture further comprises an additive selected from the group consisting of pH modifiers, viscosity modifiers, antimicrobials, colorants, healing promoters, surfactants, anti-inflammatory agents, thrombogenic agents, and radio-opaque compounds.

7. The composition according to claim 1 wherein the water-soluble carbodiimide is selected from the group consisting of compounds represented by structures 1 and 2,

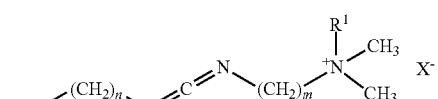

1

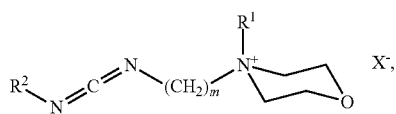

2 wherein $R^1$=hydrogen, methyl or ethyl, $R^2$=methyl, ethyl, propyl, isopropyl or cyclohexyl, n=0, 1 or 2, m=1, 2 or 3, and $X^-$=chloride, bromide, iodide, acetate, sulfate, hydrogen sulfate, methyl sulfate, methanesulfonate, ethanesulfonate, 1-propanesulfonate, 2-propanesulfonate, 1-butanesulfonate, benzenesulfonate, p-toluenesulfonate, or perchlorate.

8. The composition according to claim 1 wherein the water soluble carbodiimide is selected from the group consisting of 1-ethyl-3-(3-dimethylaminopropyl)-carbodiimide, 1-[3-(dimethylamino)propyl]-3-ethylcarbodiimide methiodide, and 1-cyclohexyl-3-(2-morpholinoethyl)carbodiimide metho-p-toluenesulfonate.

9. The composition according to claim 1 wherein the water dispersible multi-arm polyether amine is selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star copolymers of ethylene oxide and propylene oxide, amino-terminated dendritic copolymers of ethylene oxide and propylene oxide, amino-terminated comb copolymers of ethylene oxide and propylene oxide, amino-terminated star copolymers of ethylene oxide and trimethylene oxide, amino-terminated dendritic copolymers of ethylene oxide and trimethylene oxide, amino-terminated comb copolymers of ethylene oxide and trimethylene oxide, amino-terminated star copolymers of ethylene oxide and butylene oxide, amino-terminated dendritic copolymers of ethylene oxide and butylene oxide, amino-terminated comb copolymers of ethylene oxide and butylene oxide, amino-terminated star copolymers of ethylene oxide and tetrahydrofuran, amino-terminated dendritic copolymers of ethylene oxide and tetrahydrofuran, amino-terminated comb copolymers of ethylene oxide and tetrahydrofuran, amino-terminated dendritic polyamidoamines, polyoxyalkylene triamines, and mixtures thereof.

10. The composition according to claim 1 wherein the weight-average molecular weight of the water-dispersible multi-arm polyether amine is between about 2,000 and about 100,000 Daltons.

11. The composition according to claim 1 wherein the water-dispersible multi-arm polyether amine is an eight arm poly(ethylene glycol) having a molecular weight of 10,000 Daltons.

* * * * *